(12) United States Patent
Kato et al.

(10) Patent No.: US 6,656,328 B2
(45) Date of Patent: Dec. 2, 2003

(54) PROCESS FOR PREPARATION OF POLYHYDRIC ALCOHOLS

(75) Inventors: Syunsaku Kato, Kagawa (JP); Daisuke Suzuki, Tokushima (JP); Yoshiko Seo, Tokushima (JP)

(73) Assignees: National Institute of Advanced Industrial Science and Technology, Tokyo (JP); Otsuka Chemical Co., Ltd., Osaka (JP)

(*) Notice: Subject to any disclaimer, the term of this patent is extended or adjusted under 35 U.S.C. 154(b) by 0 days.

(21) Appl. No.: 10/070,877

(22) PCT Filed: Jul. 5, 2001

(86) PCT No.: PCT/JP01/05829

§ 371 (c)(1),
(2), (4) Date: Mar. 5, 2002

(87) PCT Pub. No.: WO02/02486

PCT Pub. Date: Jan. 10, 2002

(65) Prior Publication Data

US 2002/0157939 A1 Oct. 31, 2002

(30) Foreign Application Priority Data

Jul. 5, 2000 (JP) ........................................ 2000-203433

(51) Int. Cl.[7] .............................................. C07C 37/00
(52) U.S. Cl. .................................................... 204/157.9
(58) Field of Search ....................................... 204/157.9

(56) References Cited

FOREIGN PATENT DOCUMENTS

JP 7-330667 A * 12/1995

OTHER PUBLICATIONS

Varma, Rajender S., et al. (1993) *Alumina–Mediated Cleavage of a t–Butyldimethylsilyl Ethers*. Tetrahedron letters, vol. 34, No. 19, pp. 3029–3032 No month available.

Varma, Rajender S., et al. (1993) *Microwave–Assisted Deacetylation on Alumina: a Simple Deprotection Method*. J. Chem. Soc., Perkin Trans. 1, No. 9, pp. 999–1000 No month available.

Greene, Theodora W. (1981) *Protective Group in Organic Synthesis*, Chapter 3: Protection for Phenols and Catechols, pp. 87–113. No month available.

Majetich, George and Hicks, Rodgers (1995) *Applications of Microwave–Accelerated Organic Synthesis*. Radiat. Phys. Chem., Vol 45. No. 4, pp 567–579 No month available.

Schmaling, Amy, et al. (1998) *Instrumentation of Microwave–Assisted Organic Synthesis*. American Laboratory, pp. 37–40 No month available.

* cited by examiner

*Primary Examiner*—Edna Wong
(74) *Attorney, Agent, or Firm*—Knobbe, Martens, Olson & Bear LLP

(57) ABSTRACT

A process for preparing a polyhydric alcohol according to the invention comprises subjecting a polyhydric alcohol compound having protected hydroxy group(s) to microwave irradiation in the presence of basic compound(s) or acid(s) having an acid dissociation exponent (pKa) of −8 to 3 at 25° C. to remove the protecting groups of the hydroxy group of the polyhydric alcohol compound. The invention can provide an industrially advantageous process for preparing polyhydric alcohols by readily removing protecting group(s) from protected hydroxy group(s) of polyhydric alcohol compounds.

11 Claims, No Drawings

US 6,656,328 B2

PROCESS FOR PREPARATION OF POLYHYDRIC ALCOHOLS

TECHNICAL FIELD

The present invention relates to a process for the preparation of polyhydric alcohol. Specifically, the invention relates to a process for the preparation of polyhydric alcohol by removing from a polyhydric alcohol compound having protected hydroxy groups the protecting groups of the hydroxy groups.

BACKGROUND ART

Compounds having hydroxy groups are highly reactive. Among such compounds, heterocyclic, aromatic, steroid and like compounds having hydroxy groups are useful as pharmaceutical intermediates, resin materials and the like.

When producing compounds such as heterocyclic compounds having hydroxy groups, aromatic compounds having hydroxy groups, steroid compounds having hydroxy groups and the like, the hydroxy groups thereof should be protected by protecting groups because they are extremely reactive.

Etherification is a typical method of protecting hydroxy groups. In this method, alkyl groups substitute for the hydrogen atoms of the hydroxy groups.

However, a method for removing the protecting groups (dealkylation method) without affecting the core chemical structure, easy to conduct and economical enough for industrial application has not yet been found.

Among the alkyl groups, methyl group has long been known to be a very stable protecting group for hydroxy group as described in "Protective Group in Organic Synthesis, Chapter 3, pp. 87–113, Theodora W. Greene (1981)". Because of the very high stability of methyl group, demethylation must be conducted under severe conditions such as prolonged heating and the like while using expensive reagent, etc.

When demethylation is conducted under severe conditions, side reactions such as decomposition of the core chemical structure and the like occur. When the objective compound is a polyhydric alcohol compound having two or more hydroxy groups, demethylation does not completely progress and part of methylated hydroxy groups remains in the reaction system. This causes a reduced purity and a low yield of the objective compound.

Particularly, when the target compounds are steroid compounds having two or more hydroxy groups, heterocyclic compounds having two or more hydroxy groups or the like, the steroid or heterocyclic skeleton, etc. is unstable, and therefore specific reagents including aluminum halide, boron halide and the like are needed. However, these reagents are expensive and substantially impossible to recover. Furthermore, disposal of the waste liquid thereof is difficult, making these reagents unsuitable for industrial use.

Therefore, although the method of protecting hydroxy group with methyl group is advantageous in that the methyl group is stable as protecting group for hydroxy group, the application is narrowly limited.

Radiat. Phys. Chem., Vol.45, No.4, pp. 567–579 (1995) and AMERICAN LABORATORY, pp.37–40, JULY 1998, etc., disclose that demethylized compounds can be produced at a yield of about 80 to 96% by subjecting aromatic alcohols having hydroxy groups protected by methyl groups to demethylation by conducting microwave irradiation in acetic acid in the presence of 48% hydrogen bromide.

However, use of hydrogen bromide leads to the formation of byproducts which are difficult to remove, and this makes isolation and purification of the objective compounds very difficult. Therefore, the improvement in the purity of the desired compounds results in an extremely lowered yield. In addition, use of hydrogen bromide causes problems of environmental pollution, disposal of the waste after completion of the reaction and the like. Furthermore, this method requires after-treatment to be conducted by using an alkali; however, alkali treatment involves danger because it forms an unduly large amount of neutralization heat. Therefore, in practice, if crystals of the objective compounds are separated out by simply cooling the reaction mixture containing the objective compounds, the resultant crystals can be collected by filtering out and repeatedly washing the obtained crystals with water, or adding the crystals into a large volume of ice water. Employing these methods, when the objective compounds are water-soluble, makes the isolation of the objective compounds difficult. Therefore, the methods described above can be employed only when the objective compounds are compounds insoluble in water and separated out as crystals.

DISCLOSURE OF THE INVENTION

An object of the invention is to provide an industrially advantageous process for preparing polyhydric alcohols by readily removing protecting group(s) from hydroxy group(s) of polyhydric alcohol compounds wherein the hydroxy group(s) is protected.

Another object of the invention is to provide a process whereby the objected polyhydric alcohols are produced in a high yield and high purity.

A further object of the invention is to provide a process for preparing polyhydric alcohols wherein expensive and special reagents are not required and which is free from bothersome waste liquid treatment.

The inventors carried out intensive research to develop a novel process for preparing polyhydric alcohols and found that the above objects can be achieved by irradiating polyhydric alcohol compounds having protected hydroxy groups with microwaves in the presence of a basic compound or an acid having a pKa (acid dissociation exponent) of −8 to 3 at 25° C. The invention is accomplished by the above findings.

The invention provides a process for preparing polyhydric alcohol comprising the hydroxy protecting group(s) in the polyhydric alcohol compound is removed by irradiating polyhydric alcohol compound having protected hydroxy group(s) with microwaves in the presence of basic compound(s) or acid(s) having a pKa (acid dissociation exponent) of −8 to 3 at 25° C.

According to the invention, by irradiating polyhydric alcohol compound having protected hydroxy group(s) with microwaves in the presence of basic compound(s) or acid(s) having a specific acid dissociation exponent, the hydroxy protecting group(s) is removed, and thereby polyhydric alcohol compounds useful as pharmaceutical intermediates, pharmaceutical preparations and resin materials can be obtained in a short time, a high purity and a high yield without producing byproducts. Especially, when the objective polyhydric alcohol compounds are catechol, estradiol, morphine and the like, the process of the invention is advantageously employed because these compounds are used as medicines or raw materials for medicines and the purity thereof is important.

Polyhydric Alcohols

The polyhydric alcohols to be prepared by the process of the invention include heterocyclic compounds having 2 or more (preferably 2 to 6) hydroxy groups, alicyclic hydrocarbon compounds having 2 or more (preferably 2 to 6) hydroxy groups, monocyclic aromatic hydrocarbons having 2 or more (preferably 2 to 9) hydroxy groups and condensed polycyclic hydrocarbons having 2 or more (preferably 2 to 9) hydroxy groups.

Examples of heterocyclic compounds having 2 or more hydroxy groups are heterocyclic compounds having 2 to 6 hydroxy groups such as follows:

pyridines represented by the formula:

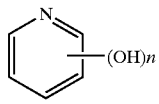

wherein n is 2 or 3, pyrimidines represented by the formula:

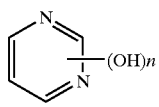

wherein n is as defined above, triazines represented by the formula:

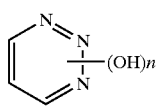

wherein n is as defined above, triazines represented by the formula:

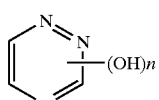

wherein n is as defined above, triazines represented by the formula:

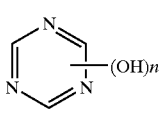

wherein n is as defined above, compounds represented by the formula:

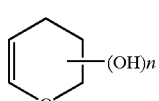

wherein n is as defined above, flavones represented by the formula:

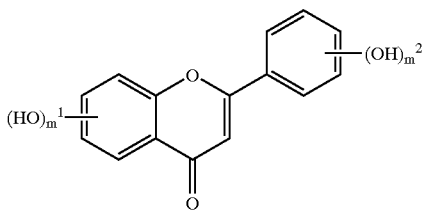

wherein $m^1$ and $m^2$ are integers from 0 to 3, with the proviso $m^1+m^2$ 2, etc.

Specific examples of such heterocyclic compounds are 2,3-dihydroxypyridine, 2,4-dihydroxypyridine, 2,5-dihydroxypyridine, 2,6-dihydroxypyridine, 3,4-dihydroxypyridine, 3,5-dihydroxypyridine, 2,4,6-trihydroxypyridine, 2,4-dihydroxypyrimidine, 2,5-dihydroxypyrimidine, 3,4-dihydroxypyrimidine, 3,5-dihydroxypyrimidine, 2,4,5-trihydroxypyrimidine, 2,4,6-trihydroxypyrimidine, 4,5,6-trihydroxypyrimidine, 4,5,6-trihydroxytriazine, 3,5,6-trihydroxytriazine, 2,4,6-trihydroxytriazine, D-glucal, 5,7-dihydroxyflavone, 4',5-dihydroxyflavone, 3',4',5-trihydroxyflavone, 4',5,7-trihydroxyflavone, 3',4',5,5'7-tetrahydroxyflavone, 3',4',5,7-tetrahydroxyflavone, 3',4',5,5',7-pentahydroxyflavone and the like.

Examples of alicyclic hydrocarbon compounds having 2 or more hydroxy groups are alicyclic hydrocarbon compounds having 2 to 6 hydroxy groups such as follows:

steroid compounds represented by the formula:

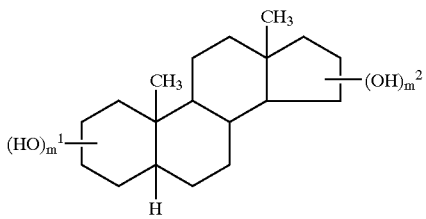

wherein $m^1$ and $m^1$ are as defined above, steroid compounds represented by the formula:

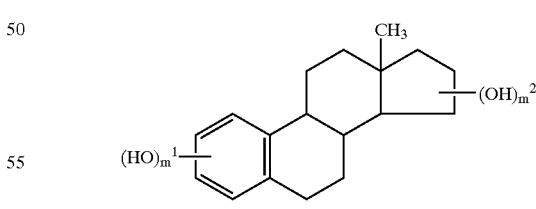

wherein $m^1$ and $m^2$ are as defined above, etc.

Specific examples of such alicyclic hydrocarbon compounds are 3,16-dihydroxyandrostane, 3,17-dihydroxyandrostane, androstane-3,16,17-triol, 3,17-dihydroxyestradiol, 3,16,17-estriol and the like.

Examples of monocyclic aromatic hydrocarbons having 2 or more hydroxy groups are monocyclic aromatic hydrocarbons having 2 to 9 hydroxy groups such as follows:

benzenes represented by the formula:

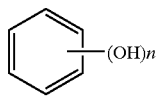

wherein n is as defined above,
carbinols represented by the formula:

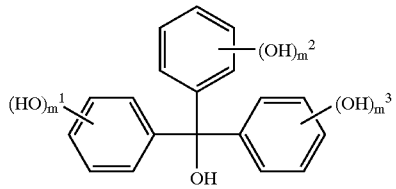

wherein $m^1$ and $m^2$ are as defined above, and $m^3$ is an integer from 0 to 3, with the proviso $m^1+m^2+m^3 \geq 2$, etc.

Examples of such monocyclic aromatic hydrocarbons are 1,2-dihydroxybenzene, 1,3-dihydroxybenzene, 1,4-dihydroxybenzene, 1,2,3-trihydroxybenzene, 1,2,4-trihydroxybenzene, 1,3,5-trihydroxybenzene, 2,2',4,4',4''-pentahydroxy triphenylcarbinol and the like.

Examples of condensed polycyclic aromatic hydrocarbons having 2 or more hydroxy groups are condensed polycyclic aromatic hydrocarbons having 2 to 9 hydroxy groups such as follows:

naphthalenes represented by the formula:

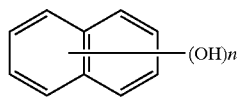

wherein n is as defined above,
triphenylenes represented by the formula:

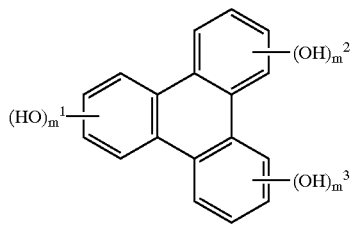

wherein $m^1$, $m^2$ and $m^3$ are as defined above, etc.

Specific examples of such condensed polycyclic aromatic hydrocarbons are 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,6-dihydroxynaphthalene, 2,7-dihydroxynaphthalene, 2,3,6,7,10,11,-hexahydroxy triphenylene and the like.

Polyhydric Alcohol Compounds Having Protected Hydroxy Groups

The present invention uses a polyhydric alcohol compound having protected hydroxy group(s) as a starting material. As long as the hydroxy groups are protected, any known polyhydric alcohol compound can be used.

According to the invention, it is not necessary that all of the hydroxy groups be protected in the polyhydric alcohol used as a starting material. Polyhydric alcohol compounds of the invention include polyhydric alcohol compounds having two hydroxy groups but only one of them being protected such as codeine, etc.

The protecting groups used for protecting hydroxy group(s) are not limited. Preferable protecting groups include at least one member selected from the group consisting of aliphatic hydrocarbon groups, alicyclic hydrocarbon groups and aromatic hydrocarbon groups.

A aliphatic hydrocarbon groups include saturated aliphatic hydrocarbon groups and unsaturated aliphatic hydrocarbon groups. Aliphatic hydrocarbon groups may be substituted with aryl groups including a phenyl group. Examples of such aliphatic hydrocarbon groups are lower alkyl groups, lower alkenyl groups and the like. Specific examples of lower alkyl groups are methyl, ethyl, n-propyl, isopropyl, n-butyl, isobutyl, tert-butyl and like $C_1$ to $C_4$ straight or branched alkyl groups, etc. Specific examples of lower alkenyl groups are vinyl, allyl and like $C_2$ to $C_4$ alkenyl groups, etc. Examples of aliphatic hydrocarbon groups substituted with an aryl group are arylalkyl groups and the like. Specific examples of arylalkyl groups are benzyl, 1-phenylethyl, 2-phenylethyl and like phenyl-$C_{1-4}$alkyl groups.

Examples of alicyclic hydrocarbon groups are cyclopentyl, cyclohexyl and like $C_3$ to $C_8$ cycloalkyl groups, etc.

Examples of aromatic hydrocarbon groups are aryl groups, etc. Specific examples of aryl groups are a phenyl group, a tolyl group and the like.

Examples of polyhydric alcohols having hydroxy groups being protected by such protecting groups are the compounds as below.

Examples of heterocyclic compounds having protected hydroxy groups are heterocyclic compounds having 2 to 6 protected hydroxy groups such as follows:

pyridines represented by the formula:

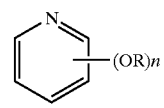

wherein R is an aliphatic hydrocarbon group, an alicyclic hydrocarbon group or an aromatic hydrocarbon group and n is as defined above, pyrimidines represented by the formula:

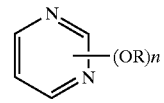

wherein R and n are as defined above,
triazines represented by the formula:

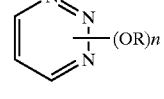

wherein R and n are as defined above, triazines represented by the formula:

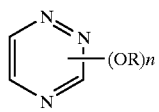

wherein R and n are as defined above,
triazines represented by the formula:

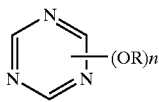

wherein R and n are as defined above,
compounds represented by the formula:

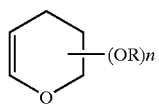

wherein R and n are as defined above,
flavones represented by the formula:

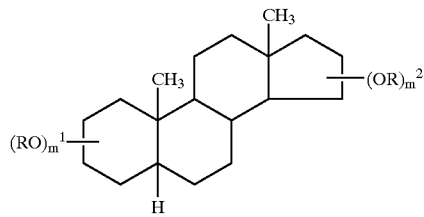

wherein R, $m^1$ and $m^2$ are as defined above, etc.

Specific examples of heterocyclic compounds having protected hydroxy groups are 2,3-dimethoxypyridine, 2,4-dimethoxypyridine, 2,5-dimethoxypyridine, 2,6-dimethoxypyridine, 3,4-dimethoxypyridine, 3,5-dimethoxypyridine, 2,4,6-trimethoxypyridine, 2,3-diethoxypyridine, 2,4-diethoxypyridine, 2,5-diethoxypyridine, 2,6-diethoxypyridine, 3,4-diethoxypyridine, 3,5-diethoxypyridine, 2,4,6-triethoxypyridine, 2,3-di-(t-butoxy)pyridine, 2,4-di-(t-butoxy)pyridine, 2,5-di-(t-butoxy)pyridine, 2,6-di-(t-butoxy)pyridine, 3,4-di-(t-butoxy)pyridine, 3,5-di-(t-butoxy)pyridine, 2,4,6-tri-(t-butoxy)pyridine, 2,3-diallyloxypyridine, 2,4-diallyloxypyridine, 2,5-diallyloxypyridine, 2,6-diallyloxypyridine, 3,4-diallyloxypyridine, 3,5-diallyloxypyridine, 2,4,6-triallyloxypyridine, 2,4-dimethoxypyrimidine, 2,5-dimethoxypyrimidine, 3,4-dimethoxypyrimidine, 3,5-dimethoxypyrimidine, 2,4,5-trimethoxypyrimidine, 2,4,6-trimethoxypyrimidine, 4,5,6-trimethoxypyrimidine, 2,4-diethoxypyrimidine, 2,5-diethoxypyrimidine, 3,4-diethoxypyrimidine, 3,5-diethoxypyrimidine, 2,4,5-triethoxypyrimidine, 2,4,6-triethoxypyrimidine, 4,5,6-triethoxypyrimidine, 2,4-di-(t-butoxy)pyrimidine, 2,5-di-(t-butoxy)pyrimidine, 3,4-di-(t-butoxy)pyrimidine, 3,5-di-(t-butoxy)pyrimidine, 2,4,5-tri-(t-butoxy)pyrimidine, 2,4,6-tri-(t-butoxy)pyrimidine, 4,5,6-tri-(t-butoxy)pyrimidine, 2,4-diallyloxypyrimidine, 2,5-diallyloxypyrimidine, 3,4-diallyloxypyrimidine, 3,5-diallyloxypyrimidine, 2,4,5-triallyloxypyrimidine, 2,4,6-triallyloxypyrimidine, 4,5,6-triallyloxypyrimidine, 4,5,6-trimethoxytriazine, 4,5,6-triethoxytriazine, 4,5,6-tri-(t-butoxy)triazine, 4,5,6-triallyloxytriazine, 3,5,6-trimethoxytriazine, 3,5,6-triethoxytriazine, 3,5,6-tri-(t-butoxy)triazine, 3,5,6-triallyloxytriazine, 2,4,6-trimethoxytriazine, 2,4,6-triethoxytriazine, 2,4,6-tri-(t-butoxy)triazine, 2,4,6-triallyloxytriazine, tri-O-benzyl-D-glucal, 5,7-dimethoxyflavone, 4',5-dimethoxyflavone, 3',4',5-trimethoxyflavone, 4',5 7-trimethoxyflavone, 3',4',5,5'-tetramethoxyflavone, 3,4',5,7-tetramethoxyflavone, 3',4',5,5',7-pentamethoxyflavone, 5-hydroxy-4'-methoxyflavone, 5-hydroxy-3',4'-dimethoxyflavone, 5-hydroxy-3',4',5'-trimethoxyflavone and the like.

Examples of alicyclic hydrocarbon compounds having protected hydroxy groups are alicyclic hydrocarbon compounds having 2 to 6 protected hydroxy groups such as follows:

steroid compounds represented by the formula:

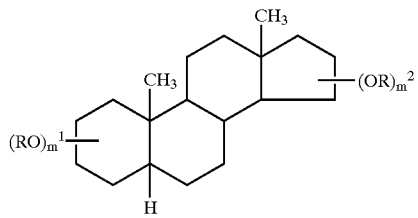

wherein R, $m^1$ and $m^2$ are as defined above,
steroid compounds represented by the formula:

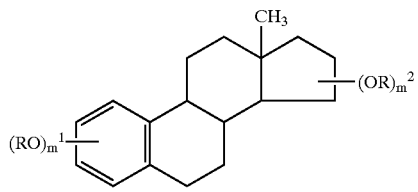

wherein R, $m^1$ and $m^2$ are as defined above, etc.

Specific examples of alicyclic hydrocarbon compounds having protected hydroxy groups are 3,16-dimethoxyandrostane, 3,17-dimethoxyandrostane, 3,16-dimethoxyandrostane, 3,16,17-trimethoxyandrostane, 3,17-dimethoxyestradiol, 3,17-diethoxyestradiol, 3,16,17-tri-O-methylerythritol and the like.

Examples of monocyclic aromatic hydrocarbons having protected hydroxy groups are monocyclic aromatic hydrocarbons having 2 to 9 protected hydroxy groups such as follows:

benzenes represented by the formula:

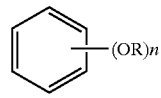

wherein R and n are as defined above, carbinols represented by the formula:

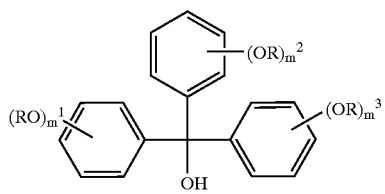

wherein R, $m^1$, $m^2$ and $m^3$ are as defined above, etc.

Specific examples of monocyclic aromatic hydrocarbons having protected hydroxy groups are 1,2-dimethoxybenzene, 1,3-dimethoxybenzene, 1,4-dimethoxybenzene, 1,2-diethoxybenzene, 1,3-diethoxybenzene, 1,4-diethoxybenzene, 1,2-di-(t-butoxy)benzene, 1,3-di-(t-butoxy)benzene, 1,4-di-(t-butoxy)benzene, 1,2-diallyloxybenzene, 1,3-diallyloxybenzene, 1,4-diallyloxybenzene, 1,2,3-trimethoxybenzene, 1,2,4-trimethoxybenzene, 1,3,5-trimethoxybenzene, 1,2,3-triethoxybenzene, 1,2,4-triethoxybenzene, 1,3,5-triethoxybenzene, 1,2,3-tri-(t-butoxy)benzene, 1,2,4-tri-(t-butoxy)benzene, 1,3,5-tri-(t-butoxy)benzene, 1,2,3-triallyloxybenzene, 1,2,4-triallyloxybenzene, 1,3,5-triallyloxybenzene, diphenyl ether, 2,2',4,4',4"-pentamethoxy triphenyl carbinol and the like.

Examples of condensed polycyclic aromatic hydrocarbons having 2 or more protected hydroxy groups are the condensed polycyclic aromatic hydrocarbons having 2 to 9 hydroxy groups such as follows:

naphthalenes represented by the formula:

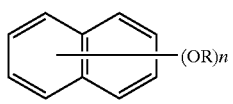

wherein R and n are as defined above, triphenylenes represented by the formula:

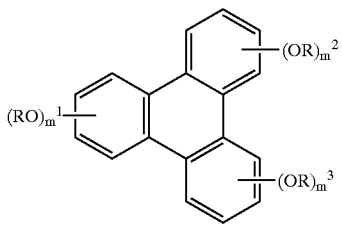

wherein R, $m^1$, $m^2$ and $m^3$ are as defined above, etc.

Specific examples of condensed polycyclic aromatic hydrocarbons having protected hydroxy groups are 1,2-dimethoxynaphthalene, 1,3-dimethoxynaphthalene, 1,4-dimethoxynaphthalene, 1,5-dimethoxynaphthalene, 1,6-dimethoxynaphthalene, 1,7-dimethoxynaphthalene, 1,8-dimethoxynaphthalene, 2,3-dimethoxynaphthalene, 2,6-dimethoxynaphthalene, 2,7-dimethoxynaphthalene, 1,2-diethoxynaphthalene, 1,3-diethoxynaphthalene, 1,4-diethoxynaphthalene, 1,5-diethoxynaphthalene, 1,6-diethoxynaphthalene, 1,7-diethoxynaphthalene, 1,8-diethoxynaphthalene, 2,3-diethoxynaphthalene, 2,6-diethoxynaphthalene, 2,7-diethoxynaphthalene, 1,2-di-(t-butoxy)naphthalene, 1,3-di-(t-butoxy)naphthalene, 1,4-di-(t-butoxy)naphthalene, 1,5-di-(t-butoxy)naphthalene, 1,6-di-(t-butoxy)naphthalene, 1,7-di-(t-butoxy)naphthalene, 1,8-di-(t-butoxy)naphthalene, 2,3-di-(t-butoxy)naphthalene, 2,6-di-(t-butoxy)naphthalene, 2,7-di-(t-butoxy)naphthalene, 1,2-diallyloxynaphthalene, 1,3-diallyloxynaphthalene, 1,4-diallyloxynaphthalene, 1,5-diallyloxynaphthalene, 1,6-diallyloxynaphthalene, 1,7-diallyloxynaphthalene, 1,8-diallyloxynaphthalene, 2,3-diallyloxynaphthalene, 2,6-diallyloxynaphthalene, 2,7-diallyloxynaphthalene, 2,3,6,7,10,11-hexamethoxyphenylene and the like.

Basic Compounds or Acids Having a PKa of −8 to 3

The reaction system of the invention requires the presence of a basic compound or an acid having a pKa (acid dissociation exponent) of −8 to 3 at 25° C. Presence of the aforementioned basic compound or acid in the reaction system enables the deprotection step to progress more smoothly, and results in an improved yield of the objective compounds.

Heretofore known acids can be used as long as they have acid dissociation exponents in the range defined above. Such acids include hydrochloric acid, nitric acid, sulfuric acid, phosphoric acid and like mineral acids, trifluoroacetic acid, monochloroacetic acid, methanesulfonic acid, trifluoromethanesulfonic acid and like organic acids, etc. When an acid with an acid dissociation exponent that does not fall in the above range, for example, acetic acid having a dissociation exponent of 4.75 is used, the object of the invention cannot be achieved. Hydrochloric acid is preferable. The aforementioned trifluororacetic acid, methanesulfonic acid and like organic acids can also be used as organic solvents as described below.

In the invention, known basic compounds can be used. Specific examples are sodium hydroxide, potassium hydroxide and like alkali metal hydroxides, calcium hydroxide and like alkaline earth metal hydroxides, triethylamine, diisopropylamine, pyridine, N,N-dimethylaniline and like organic amines, potassium tert-butoxide and like alkali metal alcoxides, etc. A preferable basic compound is sodium hydroxide.

The above acids can be used alone or in combinations. The basic compounds can also be used alone or in combinations.

The amount of acid or basic compound used is not limited and is selected from a wide range depending on various conditions including the types of starting materials, the amounts and kinds of solvents, the type of acid or basic compound, the reaction conditions (frequency and power of the microwaves, reaction temperature, reaction time, etc.) and the like. However, the amount used is generally about 0.5 to about 10 equivalent, and preferably about 1 to about 3 equivalent based on the protecting group(s) of the polyhydric alcohol compounds.

Deprotection Reaction

In the invention, the deprotection reaction (hydrolysis) whereby the protecting groups are removed from polyhydric alcohol compounds having protected hydroxy groups is generally conducted in water or a water-organic solvent mixture. The water-organic solvent mixture comprises an organic solvent and water which can be a homogeneous system or a two-phase system. When a water-organic solvent mixture is used, the ratio of water to organic solvent is not limited and is selected from a wide range depending on various conditions including the types and amounts of starting materials, the kinds of solvents, the type and amounts of acid or basic compound, the reaction conditions (frequency and power of the microwaves, reaction temperature, reaction time, etc.) and the like. However, it is preferable that water and the organic solvent are mixed in such a manner that all the protected hydroxy groups in the polyhydric alcohol compounds subjected to deprotection will be hydrolyzed, i.e., the content of water will exceed the total moles of the protected hydroxy groups. The ratio of water:organic solvent is preferably in the range of 1:100 to 100:1, and more preferably in the range of 1:10 to 10:1.

Organic solvents usable with water are not limited insofar as they do not adversely affect the reaction. Specific examples are formic acid, acetic acid, trifluoroacetic acid, methanesulfonic acid and like organic acids, ethanol, isopropyl alcohol, ethylene glycol and like alcohols, acetone, methyl ethyl ketone and like ketones, dioxane, tetrahydrofuran and like cyclic ethers, pentane, hexane, cyclohexane and like hydrocarbons, benzene, toluene and like aromatic hydrocarbons, dichloromethane, dichloroethane, chlorobenzene and like halogenated hydrocarbons, etc. They can be used singly or in combinations.

The amount of solvent (water or water-organic solvent mixture) used is not limited and is selected from a wide range depending on various conditions including the types of starting materials, the types of solvents, the type and amounts of acid or basic compound, the reaction condition (frequency and power of the microwaves, reaction temperature, reaction time, etc.) and the like. However, the amount is generally about 1 to about 10 liters, and preferably about 5 to about 50 liters per 1 kg of the starting materials.

In the invention, the frequency of the microwaves irradiating the reaction system is generally in the range of from 915 MHz to 28 GHz, preferably from 915 MHz to 5.8 GHz, and most preferably 2.45 GHz.

The power of microwave is not limited and is selected from a wide range depending on various conditions including the types and amounts of starting materials, the types and amounts of solvents, the type and amounts of acid or basic compound, the reaction conditions (frequency of the microwaves, reaction temperature, reaction time, etc.) and the like, and, generally, is in the range of from 200 to 1600 W, preferably in the range of from 400 to 1200 W. The microwave irradiation can be conducted continuously or intermittently. The microwave irradiation time depends on the frequency and the power of the microwaves, etc. and cannot be generalized, however, usually it is in the range of about 30 seconds to about 3 hours.

The reaction of the invention is conducted with or without stirring, generally at about 0° C. to about 200° C., and preferably at about 60° C. to about 160° C. The reaction time varies depending on the types and amounts of starting materials, the power of the microwaves, the reaction temperature and the like. The reaction is generally completed in about 1 minute to about 3 hours. The reaction of the invention can also be conducted under ordinary pressure. When the reaction is conducted under ordinary pressure, the temperature should not exceed the reflux temperature of the solvent, and therefore in order to complete the reaction in a short time, the reaction of the invention is preferably conducted under pressure. When the reaction pressure is too high, decomposition of starting material and objective compounds may occur, and therefore the reaction pressure is generally 0.1 to 3 MPa, and preferably 0.2 to 1 MPa.

The polyhydric alcohols obtained by the process of the invention can be readily isolated from the reaction system and purified by a general purification process.

According to the process of the invention, all the hydroxy protecting groups can be completely removed from the polyhydric alcohol compounds in a short time without being accompanied by side effects such as decomposition of the objective polyhydric alcohol compounds, etc.

By employing the process of the invention, hydroxy heterocyclic compounds, hydroxy aromatic compounds and steroid compounds useful as pharmaceutical intermediates or resin materials can be obtained in a short time, a high purity and a high yield.

The process of the invention requires neither expensive and special reagents nor troublesome waste liquid disposal.

According to the process of the invention, the objective polyhydric alcohols can be industrially and effectively produced from polyhydric alcohol compounds having protected hydroxy groups.

The process of the invention can be applied even when the objective polyhydric alcohol is water-soluble polyhydric alcohol.

BEST MODE FOR CARRYING OUT THE INVENTION

The following Examples and Comparative Examples illustrate the present invention in further detail.

EXAMPLE 1

In a 50 cc glass sealed tube, 0.751 g of 2,6-dimethoxypyridine, 18 ml of 35% hydrochloric acid and 18 ml of acetic acid were placed. In an oven-type microwave irradiator where power and temperature are controllable, the mixture was continuously irradiated with microwaves having a frequency of 2.45 GHz and a power of 400 W, and then subjected to the reaction at 140° C. and 0.51 MPa for 10 minutes. The reaction mixture was analyzed using liquid chromatography, showing a residual ratio of the starting material (2,6-dimethoxypyridine) of 0.2%, and a yield of the objective compound (2,6-dihydroxypyridine) of 98.7%.

Water (20 ml) was added to the reaction mixture, and its pH was adjusted to be 8 to 9 using a 10% sodium hydroxide aqueous solution. Thereafter, the reaction mixture was subjected to extraction twice with 50 ml of ethyl acetate. The extract was dried on anhydrous magnesium sulfate and concentrated under reduced pressure, and the resultant residue was crystallized by adding a small amount of ether, obtaining 0.558 g of the objective compound (2,6-dihydroxypyridine, yield 96%, purity 99%).

$^1$H-NMR(DMSO) δ ppm: 3.4(brs, 2H), 5.7(d,1H), 7.3(dd, 2H)

EI-MS: $M^{30}$=111

EXAMPLE 2

The treatment was conducted in the same manner as in Example 1 except that the reaction in a microwave irradiator was carried out at 120° C. and 0.31 MPa for 3 minutes while intermittently irradiating the mixture with microwaves having a frequency of 2.45 GHz and a power of 1000 W for 0.3 seconds and then pausing for 0.7 seconds. The reaction mixture was analyzed using liquid chromatography, showing a residual ratio of the starting material (2,6-dimethoxypyridine) of 1.3%, and a yield of the objective compound (2,6-dihydroxypyridine) of 99.0%.

The resultant mixture was treated in the same manner as in Example 1, obtaining 0.564 g of the objective compound (2,6-dihydroxypyridine, yield:97%, purity:99%). The obtained 2,6-dihydroxypyridine gave the same $^1$H-NMR and EI-MS as those of the 2,6-dihydroxypyridine obtained in Example 1.

COMPARATIVE EXAMPLE 1

In a 50 cc short-neck flask, 0.751 g of 2,6-dimethoxypyridine, 18 ml of 35% hydrochloric acid and 18 ml of acetic acid were placed, and then the flask was dipped in an oil bath of 140° C. while conducting stirring reflux for 1 hour. The reaction mixture was analyzed using liquid chromatography, showing a yield of 2,6-dihydroxypyridine of 28.8% and a residual ratio of the starting material (2,6-dimethoxypyridine) of 51.2%.

COMPARATIVE EXAMPLE 2

In a 50 cc glass sealed tube, 0.751 g of 2,6-dimethoxypyridine, 18 ml of 35% hydrochloric acid and 18 ml of acetic acid were placed. The tube was dipped in an oil bath of 140° C. and the mixture was subjected to the reaction at 140° C. and 0.51 MPa for 1 hour. The reaction mixture was analyzed using liquid chromatography, showing a yield of 2,6-dihydroxypyridine of 11.3% and a residual ratio of the starting material (2,6-dimethoxypyridine) of 13.4%.

EXAMPLE 3

The treatment was conducted in the same manner as in Example 1 except that 0.8304 g of 2,7-dimethoxynaphthalene was used instead of 0.751 g of 2,6-dimethoxypyridine, and the reaction was conducted for 2 minutes. The reaction mixture was analyzed using liquid chromatography, showing a yield of the objective compound (2,7-dihydroxynaphthalene) of 99.8% and a residual ratio of the starting material (2,7-dimethoxynaphthalene) of 0.0%.

EXAMPLE 4

In a 50 cc glass sealed tube, 0.8304 g of 2,7-dimethoxynaphthalene, 18 ml of 1 M sodium hydroxide aqueous solution and 18 ml of methyl ethyl ketone were placed. In an oven-type microwave irradiator where power and temperature are controllable, the mixture was continuously irradiated with microwaves having a frequency of 2.45 GHz and a power of 400 W, and then subjected to the reaction at 120° C. and 0.62 MPa for 20 minutes. The reaction mixture was analyzed using liquid chromatography, showing a yield of the objective compound (2,7-dihydroxynaphthalene) of 88.9% and a residual ratio of the starting material (2,7-dimethoxynaphthalene) of 5.9%.

The resultant mixture was subjected to the same process as in Example 1, obtaining a desired compound (2,7-dihydroxynaphthalene) having a purity of 99% at a yield of 87%.

EXAMPLE 5

In a 50 cc glass sealed tube, 0.8304 g of 2,7-dimethoxynaphthalene, 1.2 ml of 35% hydrochloric acid (equivalent of the methoxy groups) and 18 ml of acetic acid were placed. In an oven-type microwave irradiator where power and temperature are controllable, the mixture was continuously irradiated with microwaves having a frequency of 2.45 GHz and a power of 400 W, and then subjected to the reaction at 140° C. and 0.51 MPa for 2 minutes. The reaction mixture was analyzed using liquid chromatography, showing a yield of the objective compound (2,7-dihydroxynaphthalene) of 94.4% and a residual ratio of the starting material (2,7-dimethoxynaphthalene) of 0.0%.

The resultant mixture was subjected to the same process as in Example 1, obtaining an objective compound (2,7-dihydroxynaphthalene) having a purity of 99% at a yield of 93%.

COMPARATIVE EXAMPLE 3

The treatment was conducted in the same manner as in Comparative Example 1 except that 0.8304 g of 2,7-dimethoxynaphthalene was used instead of 0.751 g of 2,6-dimethoxypyridine. The reaction mixture was analyzed using liquid chromatography, showing a yield of the objective compound (2,7-dihydroxynaphthalene) of 74.7% and a residual ratio of the starting material (2,7-dimethoxynaphthalene) of 0.0%.

COMPARATIVE EXAMPLE 4

The test was conducted in the same manner as in Comparative Example 2 except that 0.8304 g of 2,7-dimethoxynaphthalene was used instead of 0.751 g of 2,6-dimethoxypyridine. The reaction mixture was analyzed using liquid chromatography, showing a yield of the objective compound (2,7-dihydroxynaphthalene) of 81.2% and a residual ratio of the starting material (2,7-dimethoxynaphthalene) of 0.0%.

EXAMPLE 6

In a 50 cc glass sealed tube, 3.6 g of 2,3,6,7,10,11-hexamethoxytriphenylene, 20 ml of 35% hydrochloric acid and 20 ml of acetic acid were placed. In an oven-type microwave irradiator where power and temperature are controllable, the mixture was continuously irradiated with microwaves having a frequency of 2.45 GHz and a power of 800 W, and then subjected to the reaction at 140° C. and 0.51 MPa for 2 hours. The reaction mixture was analyzed using liquid chromatography, showing a yield of the objective compound (2,3,6,7,10,11-hexahydroxytriphenylene) of 90.8% and a residual ratio of the starting material (2,3,6,7,10,11-hexamethoxytriphenylene) of 0.0%.

Pouring this mixture into 100 ml of ice water produces the objective 2,3,6,7,10,11-hexahydroxytriphenylene in the form of crystal (purity:99%, yield:90%).

$^1$H-NMR(DMSO-$d_6$) δ ppm: 7.605 (brs, 6H), 9.292(brs, 6H)

$^{13}$C-NMR(DMSO-$d_6$) δ ppm: 139.86, 153.96, 177.46

EXAMPLE 7

In a 50 cc glass sealed tube, 3.6 g of 2,3,6,7,10,11-hexamethoxytriphenylene, 20 ml of 35% hydrochloric acid and 20 ml of acetic acid were placed. In an oven-type microwave irradiator where power and temperature are controllable, the mixture was subjected to the reaction for 2 hours at 140° C. and 0.51 MPa by intermittently irradiating the mixture with microwaves having a frequency of 2.45 GHz and a power of 1200 W for 0.5 seconds and then pausing for 0.5 seconds. The reaction mixture was analyzed using liquid chromatography, showing a yield of the objective compound (2,3,6,7,10,11-hexahydroxytriphenylene) of 92.3% and a residual ratio of the starting material (2,3,6,7,10,11-hexamethoxytriphenylene) of 0.0%.

Pouring this mixture into 100 ml of ice water produces the objective compound (2,3,6,7,10,11-hexahydroxytriphenylene) in the form of crystal (purity:99%, yield:92%).

The $^1$H-NMR and $^{13}$C-NMR of the obtained 2,3,6,7,10,11-hexahydroxytriphenylene are the same those of 2,3,6,7,10,11-hexahydroxytriphenylene obtained in Example 6.

COMPARATIVE EXAMPLE 5

In a 50 cc eggplant-type flask, 3.6 g of 2,3,6,7,10,11-hexamethoxytriphenylene, 20 ml of 35% hydrochloric acid and 20 ml of acetic acid were placed, and the flask was dipped in an oil bath of 140° C. and the mixture was subjected to 36-hour of reflux while stirring. The reaction mixture was analyzed using liquid chromatography, showing a residual ratio of the starting material (2,3,6,7,10,11-hexamethoxytriphenylene) of 100.0% and no trace of the objective compound (2,3,6,7,10,11-hexahydroxytriphenylene).

COMPARATIVE EXAMPLE 6

In a 50 cc glass sealed tube, 3.6 g of 2,3,6,7,10,11-hexamethoxytriphenylene, 20 ml of 35% hydrochloric acid and 20 ml of acetic acid were placed and subjected to the reaction at 140° C. and 0.51 MPa for 2 hours. Thereafter, the reaction mixture was analyzed using liquid chromatography, showing a residual ratio of the starting material (2,3,6,7,10,11-hexamethoxytriphenylene) of 100% and no trace of the objective compound (2,3,6,7,10,11-hexahydroxytriphenylene).

EXAMPLE 8

In a 50 cc glass sealed tube, 3.0 g of 3,17-dimethoxyestradiol, 20 ml of 35% hydrochloric acid and 20 ml of acetic acid were placed. In an oven-type microwave irradiator where power and temperature are controllable, the mixture was subjected to the reaction at 120° C. and 0.62 MPa for 5 minutes by continuously irradiating microwaves having a frequency of 2.45 GHz and a power of 400 W. Then, the reaction mixture was poured into water, subjected to extrusion with methylene chloride, dried on magnesium sulfate anhydride, concentrated and purified by column chromatography using silica gel, producing 2.7 g of estradiol (purity:99%, yield:79.7%).

EXAMPLE 9

Five millimoles of the polyhydric alcohol compounds having protected hydroxy groups which are listed on Table 1 were subjected to deprotection under the reaction conditions in Table 1 (the reaction temperature was unified to be 140° C.), producing polyhydric alcohol compounds. In Table 1, the yield of the polyhydric alcohol compounds is expressed as the objective yield.

Note that, the objective yield is the area ratio of the resultant compound to the standard object measured using liquid chromatography.

TABLE 1

| No | Polyhydric alcohol comp. with protection groups | Acid and solvent (ml/ml) | Pres. (MPa) | Microwave irr. cond. | Time (Min.) | Object. yield (%) |
|---|---|---|---|---|---|---|
| 1 | 1,2,3-trimethoxy benzene | 35% hydrochloric acid/acetic acid (15/15) | 0.62 | 800 W continuous | 10 | 95.5 |
| 2 | 2,7-dimethoxy naphthalene | 10% nitric acid/acetic acid (15/15) | 0.59 | As above | 10 | 93.9 |
| 3 | As above | 10% sulfuric acid/acetic acid (15/15) | 0.57 | As above | 10 | 88.3 |
| 4 | As above | Methanesulfonic acid/acetic acid (15/15) | 0.67 | As above | 40 | 86.2 |
| 5 | As above | Trifluoroacetic acid/acetic acid (15/15) | 0.73 | As above | 40 | 80.0 |
| 6 | As above | 50% phosphoric acid/acetic acid (15/15) | 0.58 | As above | 40 | 80.1 |
| 7 | As above | 35% hydrochloric acid/acetic acid (15/15) | 0.62 | As above | 2 | 100 |
| 8 | 2,6-di-tert-butoxypyridine | 35% hydrochloric acid/acetic acid (15/15) | 0.62 | 400 W continuous | 5 | 99.7 |
| 9 | 2,4,6-trimethoxy pyridine | 35% hydrochloric acid/acetic acid (15/15) | 0.62 | As above | 10 | 93.5 |
| 10 | 2,4,6-triallyl oxypyridine | 35% hydrochloric acid/acetic acid (15/15) | 0.62 | As above | 10 | 99.0 |
| 11 | Tri-O-benzyl-D-glucal | 35% hydrochloric acid/acetic acid (15/15) | 0.62 | As above | 10 | 85.0 |
| 12 | 2,3,6,7,10,11-hexamethoxy triphenylene | 35% hydrochloric acid/dichloroethane (15/15) | 0.95 | 800 W continuous | 120 | 80.0 |
| 13 | As above | 35% hydrochloric acid/toluene (15/15) | 0.65 | As above | 120 | 89.8 |
| 14 | As above | 35% hydrochloric acid/dioxane (15/15) | 0.55 | As above | 120 | 90.0 |

What is claimed is:

1. A process for preparing a polyhydric alcohol comprising:
   subjecting a polyhydric alcohol compound having hydroxy group(s) protected by protecting group(s) to microwave irradiation in the presence of basic compound(s) or acid(s) having an acid dissociation exponent (pKa) of −8 to 3 at 25° C. remove said protecting group(s) from said polyhydric alcohol compound, thereby obtaining a desired polyhydric alcohol.

2. The process according to claim 1, wherein said desired polyhydric alcohol obtained is one of heterocyclic compounds having 2 or more hydroxy groups, alicyclic hydrocarbon compounds having 2 or more hydroxy groups, monocyclic aromatic hydrocarbons having 2 or more hydroxy groups or condensed polycyclic aromatic hydrocarbons having 2 or more hydroxy groups.

3. The process according to claim 1, wherein said protecting group is at least one member selected from the group consisting of aliphatic hydrocarbon groups, alicyclic hydrocarbon groups and aromatic hydrocarbon groups.

4. The process according to claim 3, wherein said aliphatic hydrocarbon groups are at least one member selected from the group consisting of lower alkyl groups, lower alkenyl groups and arylalkyl groups.

5. The process according to claim 1, wherein the basic compound is at least one member selected from the group consisting of alkali metal hydroxides, alkaline earth metal hydroxides, amines and alkali metal alcoxides.

6. The process according to claim 5, wherein the basic compound is an alkali metal hydroxide.

7. The process according to claim 1, wherein the acid having an acid dissociation exponent (pKa) of −8 to 3 at 25° C. is at least one member selected from the group consisting of hydrochloric acid, nitric acid, sulfuric acid, phosphoric acid, trifluoroacetic acid, monochloroacetic acid, methanesulfonic acid and trifluoromethanesulfonic acid.

8. The process according to claim 7, wherein the acid having an acid dissociation exponent (pKa) of −8 to 3 at 25° C. is hydrochloric acid.

9. The process according to claim 1, wherein the frequency of the microwaves is in the range from 915 MHz to 28 GHz.

10. The process according to claim 1, wherein the frequency of the microwaves is in the range from 915 MHz to 5.8 GHz.

11. The process according to claim 1, wherein the power of the microwaves is in the range from 200 W to 1600 W.

* * * * *